(12) United States Patent
DiCarlo

(10) Patent No.: US 7,344,561 B2
(45) Date of Patent: *Mar. 18, 2008

(54) MONITORING SYSTEM FOR REMOTE DETECTION OF ENDOLEAKS AND/OR CHANGES IN MORPHOLOGY OF IMPLANTED ENDOLUMINAL DEVICES

(75) Inventor: Paul DiCarlo, Middleboro, MA (US)

(73) Assignee: Boston Scientific Scimed, Inc., Maplegrove, MN (US)

(*) Notice: Subject to any disclaimer, the term of this patent is extended or adjusted under 35 U.S.C. 154(b) by 861 days.

This patent is subject to a terminal disclaimer.

(21) Appl. No.: 10/635,789

(22) Filed: Aug. 6, 2003

(65) Prior Publication Data

US 2004/0098093 A1 May 20, 2004

Related U.S. Application Data

(62) Division of application No. 09/896,864, filed on Jun. 29, 2001, now Pat. No. 6,702,847.

(51) Int. Cl.
*A61F 2/06* (2006.01)
(52) U.S. Cl. .................. 623/1.34; 623/1.3; 600/309
(58) Field of Classification Search ...... 623/1.11–1.38; 600/309, 423
See application file for complete search history.

(56) References Cited

U.S. PATENT DOCUMENTS

| | | | |
|---|---|---|---|
| 4,513,049 A | 4/1985 | Yamasaki et al. | |
| 4,612,915 A | 9/1986 | Hough et al. | |
| 4,975,581 A * | 12/1990 | Robinson et al. | 250/339.09 |
| 5,134,281 A | 7/1992 | Bryenton et al. | |
| 5,195,375 A | 3/1993 | Tenerz et al. | |
| 5,205,286 A | 4/1993 | Soukup et al. | |
| 5,320,098 A | 6/1994 | Davidson | |
| 5,320,100 A | 6/1994 | Herweck et al. | |
| 5,321,257 A | 6/1994 | Danisch | |
| 5,517,998 A | 5/1996 | Madison | |
| 5,807,258 A | 9/1998 | Cimochowski et al. | |

(Continued)

FOREIGN PATENT DOCUMENTS

EP 0 897 690 2/1999

(Continued)

OTHER PUBLICATIONS

U.S. Appl. No. 09/896,822, filed Jun. 29, 2001, Haarala et al.

(Continued)

*Primary Examiner*—Suzette Gherbi
(74) *Attorney, Agent, or Firm*—Ratner Prestia

(57) ABSTRACT

An endoluminal device including a prosthesis and at least one indicator member affixed to the prosthesis that can be remotely monitored to indicate a change in pressure or morphology of the prosthesis. The indicator member may be an optical fiber, a strain gauge, or a first material having a first magnetic resonance imaging (MRI) susceptibility value that contrasts with a second MRI susceptibility value of a second material that comprises one or more remaining members of the prosthesis. A prosthesis monitoring system includes an endoluminal device as well as a subcutaneous electronics package and external electronics. Methods of detecting endoleaks or changes in morphology involve implanting an endoluminal device with the indicator and detecting information from the indicator.

33 Claims, 4 Drawing Sheets

U.S. PATENT DOCUMENTS

| | | | |
|---|---|---|---|
| 5,824,042 A | 10/1998 | Lombardi et al. | |
| 5,846,247 A | 12/1998 | Unsworth et al. | |
| 5,987,352 A | 11/1999 | Klein et al. | |
| 6,052,613 A | 4/2000 | Takaki | |
| 6,053,873 A | 4/2000 | Govari et al. | |
| 6,159,156 A | 12/2000 | Van Bockel | |
| 6,203,568 B1 | 3/2001 | Lombardi et al. | |
| 6,231,516 B1 | 5/2001 | Keilman et al. | |
| 6,280,385 B1* | 8/2001 | Melzer et al. | 600/423 |
| 6,293,966 B1 | 9/2001 | Frantzen | |
| 6,416,474 B1* | 7/2002 | Penner et al. | 600/309 |
| 6,442,413 B1 | 8/2002 | Silver | |
| 6,463,317 B1 | 10/2002 | Kucharczyk et al. | |
| 6,475,169 B2 | 11/2002 | Ferrera | |
| 6,475,170 B1 | 11/2002 | Doron et al. | |
| 6,475,222 B1 | 11/2002 | Berg et al. | |
| 6,477,426 B1 | 11/2002 | Fenn et al. | |
| 6,485,512 B1 | 11/2002 | Cheng | |
| 6,486,588 B2 | 11/2002 | Doron et al. | |
| 6,511,325 B1 | 1/2003 | Lalka et al. | |
| 6,702,847 B2* | 3/2004 | DiCarlo | 623/1.34 |
| 6,840,956 B1* | 1/2005 | Wolinsky et al. | 623/1.13 |
| 2001/0026111 A1 | 10/2001 | Doron et al. | |
| 2002/0045921 A1 | 4/2002 | Wolinsky et al. | |

FOREIGN PATENT DOCUMENTS

| | | |
|---|---|---|
| WO | WO 00/32092 | 6/2000 |
| WO | WO 02/00118 | 1/2002 |

OTHER PUBLICATIONS

The Invitation to Pay Additional Fees dated Oct. 25, 2002, including the partial international search results from corresponding Application No. PCT/US02/19990.

Schenck, John F., "The role of magnetic susceptibility in magnetic resonance imaging: MRI magnetic compatability of the first and second kinds," Med. Phys., 23 (6), Jun. 1996, pp. 815 and 825-824.

Paula, Greg, "MEMS sensors branch out," article abstract, from the Mechanical Engineering magazine website at "http://www.memagazine.org/backissues/October 1996/features/mems/mems.html." printed on Dec. 8, 2000.

Selvarajan, A., "Fiber Optic Sensors and Their Applications," from the National Technology University website at "http://www.ntu.edu.sg/mpe/research/programmes/sensors/sensors/fos/fosselva.htm," printed on Dec. 15, 2000.

Product description of "FOP-M In-vivo Sensor," from Fiso Technologies website at "http://fiso.com/page_fopmem.htm," printed Mar. 19, 2001.

"Micro-Measurements Strain Gages: Three-Element Rosette Pattern," from Measurements Group website at http://www.measurementsgroup.com/gages/mmter.htm.: printed Dec. 15, 2000.

"Fiber-optic transducer aids heart monitoring," (originial published in Engineering News, Jun. 7, 1999), printed from "http://www.manufacturing.net/magazine/dn/archives/1999/dn0607.99/new.html" on Dec. 8, 2000.

* cited by examiner

MONITORING SYSTEM FOR REMOTE DETECTION OF ENDOLEAKS AND/OR CHANGES IN MORPHOLOGY OF IMPLANTED ENDOLUMINAL DEVICES

This application is a Divisional Application of U.S. patent application Ser. No. 09/896,864, filed Jun. 29, 2001 now U.S. Pat. No. 6,702,847.

TECHNICAL FIELD

This invention relates generally to endoluminal devices, such as stents, grafts, and/or prostheses and, more specifically, to the detection of endoleaks or changes in morphology after implantation of a prosthesis.

BACKGROUND OF THE INVENTION

A stent is an elongated device used to support an intraluminal wall. In the case of a stenosis, a stent provides an unobstructed conduit for blood in the area of the stenosis. Such a stent may also have a prosthetic graft layer of fabric or covering lining the inside or outside thereof, such a covered stent being commonly referred to in the art as an intraluminal prosthesis, an endoluminal or endovascular graft (EVG), or a stent-graft.

A prosthesis may be used, for example, to treat a vascular aneurysm by removing the pressure on a weakened part of an artery so as to reduce the risk of rupture. Typically, a prosthesis is implanted in a blood vessel at the site of a stenosis or aneurysm endolumninally, i.e. by so-called "minimally invasive techniques" in which the prosthesis, restrained in a radially compressed configuration by a sheath or catheter, is delivered by a deployment system or "introducer" to the site where it is required. The introducer may enter the body through the patient's skin, or by a "cut down" technique in which the entry blood vessel is exposed by minor surgical means. When the introducer has been threaded into the body lumen to the prosthesis deployment location, the introducer is manipulated to cause the prosthesis to be ejected from the surrounding sheath or catheter in which it is restrained (or alternatively the surrounding sheath or catheter is retracted from the prosthesis), whereupon the prosthesis expands to a predetermined diameter at the deployment location, and the introducer is withdrawn. Stent expansion may be effected by spring elasticity, balloon expansion, or by the self-expansion of a thermally or stress-induced return of a memory material to a pre-conditioned expanded configuration. Various types of stent architectures are known in the art, including many designs comprising a filament or number of filaments, such as a wire or wires, wound or braided into a particular configuration.

One common application for the implantation of prostheses is for treatment of abdominal aortic aneurysms (AAA). AAA stents are typically placed into the aorta and iliac bifurcation with a covering to isolate the aneurysm from the blood. After the aneurysm has been isolated for some time, endoleaks may occur due to worn fabric or other reasons. Because the isolated aneurysm has become weak as a result of being isolated, once the leak starts, blood flow and pressure is slowly restored to the aneurysm, and the aneurysm may rupture. Currently, leaks are detected during follow-up angiograms and MRIs, but if the follow up visit does not coincide with the duration of time within which the leak must be treated, the undetected endoleak may result in a ruptured aneurysm that is fatal to the patient. Another method of detecting an endoleak is checking the aortic pressure with respect to the aneurysm sac pressure. This can be accomplished by introducing a pressure-sensing needle into the aneurysm sac through the skin while checking the aortic pressure using an invasive procedure.

In addition to endoleaks, other problems may also ensue after implantation of a prosthesis that can cause problems if undetected. For example, after the aneurysm is isolated, the morphology of the prosthesis may change as the aneurysm shrinks. The changing morphology may lead to iliac occlusions that occur with little to no forewarning. Current non-invasive monitoring techniques are not always successful in detecting such changing morphology.

Thus, there is a need in the art to provide non-invasive means of detecting endoleaks and/or the changing morphology of implanted prostheses.

SUMMARY OF THE INVENTION

The invention comprises an endoluminal device comprising a prosthesis having at least one indicator member affixed to the prosthesis, such as woven into or attached to the stent or graft or sandwiched therebetween, that is adapted to be remotely monitored to indicate a change in pressure or morphology of the prosthesis. The indicator member may comprise an optical fiber, a strain gauge, or a first material having a first magnetic resonance imaging (MRI) susceptibility value that contrasts with a second MRI susceptibility value of a second material that comprises one or more remaining members of the prosthesis.

The invention also comprises a prosthesis monitoring system, and a subassembly therefor, comprising a prosthesis for implantation in a lumen, the prosthesis comprising at least a first optical fiber member having a first end affixed to the prosthesis and a second end. The system further comprises means for sending an input optical signal through the optical fiber and receiving an output optical signal, such means attached to the first optical fiber second end. A transmitter may be used to transfer the information related to the return signal to a remote receiver. Where the prosthesis is deployed to isolate an aneurysm having an aneurysm sac, the system may further comprise a second optical fiber having a first end deployed in the aneurysm sac and a second end connected to the means sending signals. The means for sending/receiving signals and the transmitter may be subcutaneously implanted, thus forming an implantable subassembly. The subassembly may further comprise a subcutaneously implantable battery for supplying power to the system and a remotely-activatable, subcutaneously implantable switch for turning power on and off to the system from the battery. The subassembly may cooperate with external electronics for displaying the data externally. The first optical fiber may be configured to measure bending of the optical fiber, or the first, and optionally the second, optical fiber may be configured to measure pressure at the first end of the optical fiber.

The invention further comprises a prosthesis monitoring system at least partially implantable within a body for detecting a change in morphology of an implanted prosthesis. The morphology change detection system comprises an indicator affixed to the prosthesis and adapted to indicate the change in morphology in a remotely measurable manner, and remote monitoring means for detecting the indication of the change in morphology indicated by the indicator. In one embodiment, the indicator may comprise at least one member integral to the prosthesis that has a first magnetic resonance imaging (MRI) susceptibility value that contrasts with a second MRI susceptibility value of a second material that comprises one or more remaining members of the prosthesis, the member having a configuration adapted to change in response to the change in morphology. In this embodiment, the remote monitoring means comprises a MRI device adapted to detect the configuration of the member. In other embodiments, the system comprises an implantable optical fiber for conveying information from the indicator to the remote monitoring means.

The invention also comprises a prosthesis monitoring system at least partially implantable within a body for detecting an endoleak in an implanted prosthesis. The endoleak detection system comprises an implantable indicator adapted to indicate a change in pressure attributable to an endoleak and remote monitoring means for detecting the indication of the change in pressure provided by the indicator. The indicator may be affixed to the prosthesis, such as a strain gauge or the indicator may be adapted to be deployed in or on the aneurysm sac. In one embodiment, the indicator comprises a first optical fiber member adapted to be mounted in the aneurysm sac to detect pressure and the system further comprises means for sending at least a first input optical signal and receiving at least a first output optical signal through at least the first optical fiber. In one embodiment, the indicator consists only of the pressure-detecting optical fiber member in the aneurysm sac, but in another embodiment, the indicator comprises at least a second pressure-detecting optical fiber member affixed to the prosthesis. In this embodiment, the signal means is further adapted to send a second input optical signal and receive a second output optical signal through the second optical fiber.

The invention also comprises methods for using the systems described herein. A method for detecting a change in morphology of a prosthesis implanted within a body comprises implanting the prosthesis in a lumen of the body, the prosthesis comprising an indicator affixed thereto and adapted to indicate the change in morphology of the prosthesis. The change in morphology indicated by the indicator is detected by remote monitoring means outside the body. Where the indicator comprises a first MRI-susceptible material that contrasts with a second MRI-susceptible material that comprises one or more remaining members of the prosthesis, the monitoring step comprises first using an MRI device to perform a first MRI procedure and record a result thereof as a baseline morphology. Then, the MRI device is used to perform a subsequent MRI procedure, and a result of the subsequent MRI procedure is compared to the baseline morphology to determine if there has been any change in morphology.

A method for detecting an endoleak in an implanted prosthesis comprises the steps of implanting the prosthesis in a body lumen and implanting a monitoring system comprising an indicator for detecting a change in aneurysm sac pressure, the indicator in communication with means for conveying information from the indicator to a remote monitor outside the body. The method further comprises activating the monitoring system to cause the indicator to communicate with the means for conveying and to cause the means for conveying to transmit information to the remote monitoring means. The method may comprise implanting the prosthesis to isolate an aneurysm that comprises an aneurysm sac, and deploying a first optical fiber in the aneurysm sac.

Where the indicator consists only of the first optical fiber, the method may further comprise periodically monitoring pressure measured using the first optical fiber over a period of time sufficient to establish a baseline profile and then monitoring changes from the baseline profile, interpreting a change from the baseline profile greater than a threshold value as an indication of an endoleak. Where the prosthesis further comprises a second optical fiber integral to the stent and coupled to the monitoring system, the method may further comprise periodically monitoring a differential pressure between the first optical fiber and the second optical fiber and interpreting a change in the differential pressure greater than a threshold pressure as an indication of an endoleak.

BRIEF DESCRIPTION OF DRAWINGS

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures.

DETAILED DESCRIPTION OF INVENTION

The invention will next be illustrated with reference to the figures wherein similar numbers indicate the same elements in all figures. Such figures are intended to be illustrative rather than limiting and are included herewith to facilitate the explanation of the apparatus of the present invention.

One aspect of this invention may generally be described as an endoluminal device comprising a prosthesis and at least one indicator member affixed to the prosthesis that is adapted to be remotely monitored to indicate a change in pressure or morphology of the prosthesis. As used herein, the term "affixed" shall mean attached in any way such as made integral with or appended after individual assembly. Another aspect of the invention comprises a prosthesis monitoring system at least partially implantable within the body (or an implantable "subassembly") for detecting a change in morphology of an implanted prosthesis. The system generally comprises an indicator directly attached to the prosthesis for indicating the change in morphology of the prosthesis in a remotely measurable manner; and remote monitoring means for detecting the indication of the change in morphology provided by the indicator.

Yet another aspect of the invention comprises a prosthesis monitoring system at least partially implantable within a body for detecting an endoleak in an implanted prosthesis. The system comprises an implantable indicator for indicating a change in pressure attributable to an endoleak and remote monitoring means for detecting the indication of the change in pressure provided by the indicator.

These various general aspects of the invention may be best understood in light of a number of exemplary embodiments. For example, the indicator member may comprise an optical fiber, a strain gauge, or a first material having a first magnetic resonance imaging (MRI) susceptibility value that contrasts with a second MRI susceptibility value of a second material that comprises one or more remaining members of the prosthesis. Each embodiment has a number of possible configurations and methods for using the configuration, examples of which are presented below for illustration without limitation.

Optical Fiber Embodiments

Figure 1:
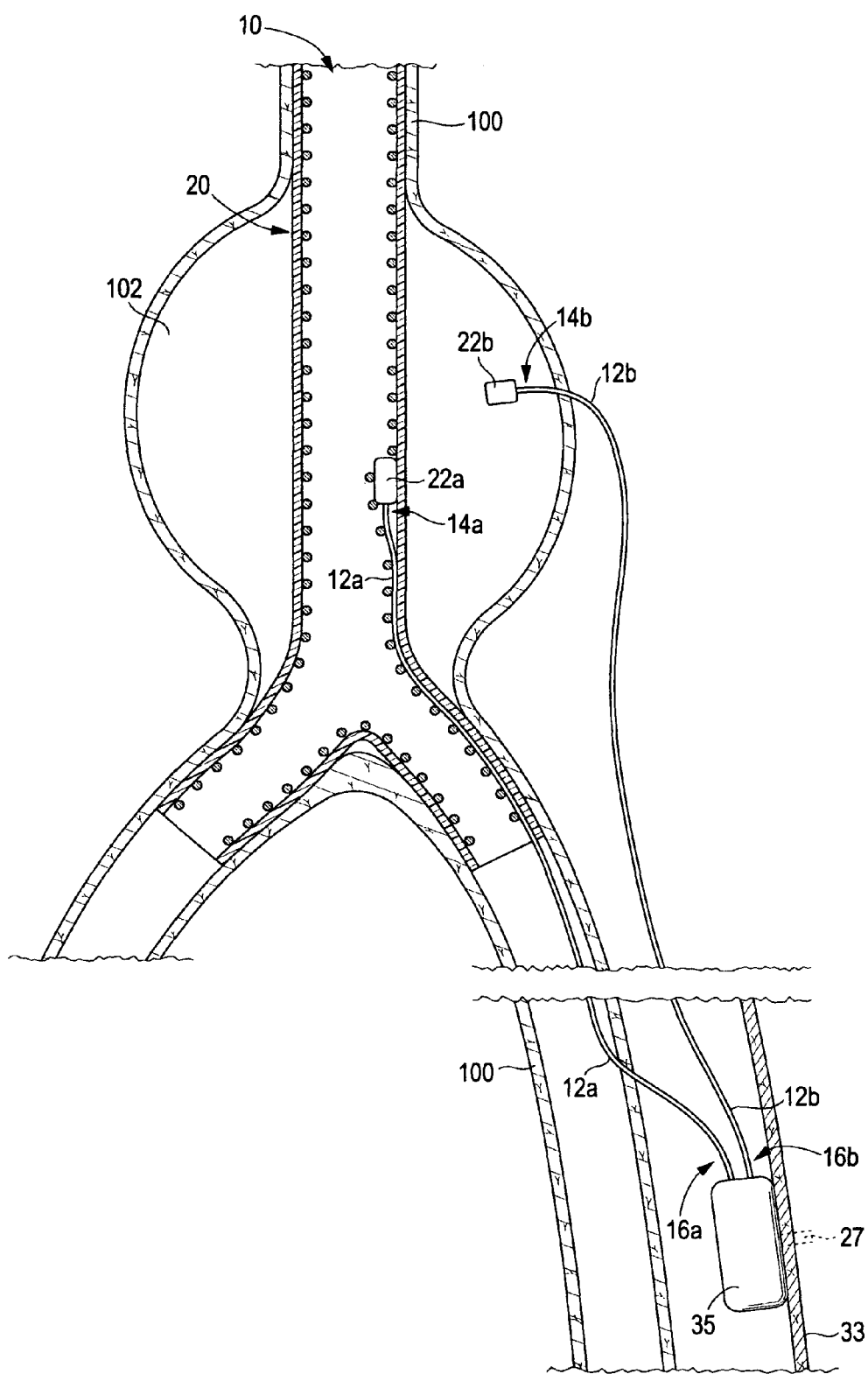
FIG. 1 is a longitudinal cross-sectional illustration of an aneurysm in a lumen and an exemplary endoluminal device of the present invention implanted therein and an exemplary monitoring system of the present invention installed to monitor the implanted device.

FIG. 1 shows a partial cross section of an endoluminal device 20 according to the present invention. Endoluminal device 20 includes a prosthesis 10 implanted within a lumen 100 to repair an aneurysm 102 and a fiber optic sensor 22a at the distal end 14a of an optical fiber 12a. Device 20 is part of an internal monitoring system, which is implanted to monitor prosthesis 10 and aneurysm 102. Proximal end 16a of fiber 12a is disposed outside of lumen 100 and is attached to subcutaneous electronics package 35, which is attached below skin 33 of the patient. The mounting location for subcutaneous electronics may be the abdomen, chest, or any location where the electronics may be comfortably and safely mounted on or within a patient.

Figure 2:
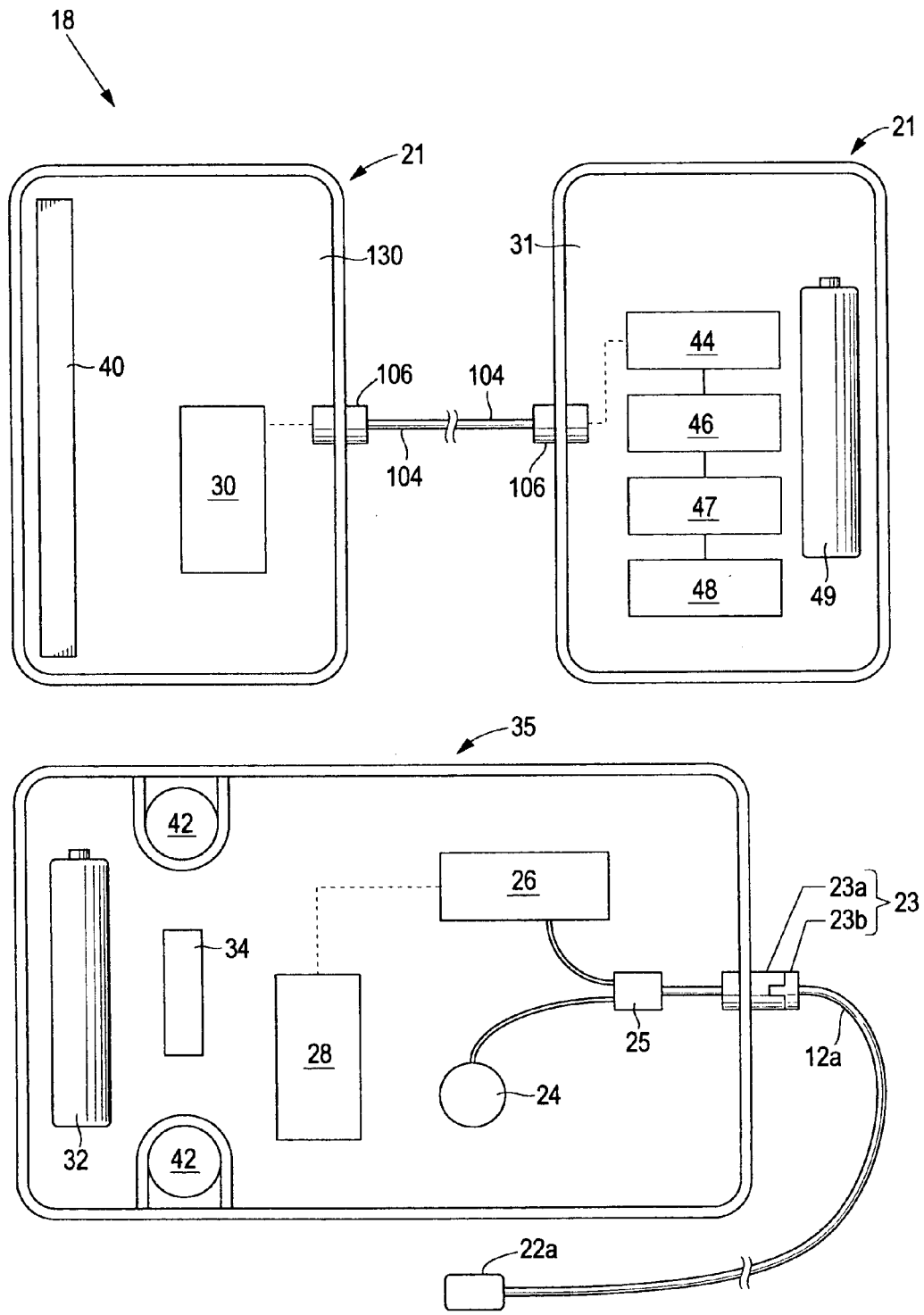
FIG. 2 is a schematic illustration of an exemplary fiber optic monitoring system of the present invention, showing exemplary subcutaneous electronics and external electronics.

FIG. 2 schematically illustrates exemplary electronic components of an exemplary prosthesis monitoring system 18, including an exemplary subcutaneous electronics package 35. Subcutaneous electronics package 35 comprises a light source 24 for sending a signal down optical fiber 12a and a spectrometer 26 to receive the return signal from optic sensor 22a. Coupler 25 allows the same fiber to be used for both sending and receiving optical signals. Light source 24 may comprise any light source suitable for use with an optical fiber as is known in the art, such as a light emitting diode (LED) or a laser source. Although the optical signal generated by such light sources is typically a signal visible to the human eye, a light signal of any wavelength may be used. Although light source 24, coupler 25, and spectrometer 26 are shown in the embodiment in FIG. 2, any suitable means or components for sending and receiving a signal through an optical fiber may be used. Optical fiber 12a is connected to subcutaneous electronics package 35 by two-part connector 23, one part 23a of the connector mounted to the electronics package and the mating part 23b mounted to fiber 12a.

The internal monitoring system further comprises a telemetric transmitter 28 in communication with spectrometer 26 for transferring information to a remote receiver 30. Transmitter 28 may transmit any type of signal capable of traveling through human skin, such as an electromagnetic signal or an optical signal. Light source 24, spectrometer 26, and output transmitter 28 are powered by a battery 32. To conserve energy, implanted battery 32 can be turned on and off via remotely-activatable switch 34, such as a magnetic switch, also known as a Hall-effect sensor. A switch operated by electromagnetic waves transmissible through the skin, or any other type of remotely-activatable switch may also be used.

Prosthesis monitoring system 18 further comprises external electronics 21, including remote receiver unit 130 and data processor 31, which may be separate units connected by cable 104 and connectors 106 as shown in FIG. 2, or a single unit (not shown). Remote receiver unit 130 comprises a bar magnet 40 which is used in conjunction with round magnets 42 in subcutaneous electronics 35 to align remote receiver 30 over transmitter 28 and to activate magnetic switch 34.

Data processor 31 comprises an analog-to-digital (a/d) converter 44 for converting analog information received by receiver 30 into digital information that may be stored in central processing unit (CPU)/memory unit 46. Data processor 31 further comprises a display driver 47 and a corresponding display 48, as well as a battery 49 for powering the data processor. The internal components of data processor 31 may comprise more or fewer components than shown in FIG. 2, however, and may include any number of components necessary to convert the signal received by receiver 30 to a usable form for monitoring the prosthesis.

The information transferred by output transmitter 28 may be raw information relating to the signal received by spectrometer 26, or subcutaneous electronics 35 may include an a/d converter and/or a CPU/memory unit to enable the subcutaneous system to analyze data continuously or on some periodic basis, and log that data and/or analysis. Implantable devices for monitoring physiological events are known generally in the art, as described in U.S. Pat. No. 5,987,352 to Klein et al., incorporated herein by reference. Where data analysis is continuously performed, it may not be desirable for subcutaneous electronics to have a switch 34, but instead to have a battery charger to allow recharging of battery 32 from outside the body inductively or through the use of electromagnetic energy. A recharging port may also protrude through the patient's skin to allow a direct connection. Switchless operation and battery recharging capability may be provided for systems even without continuous data monitoring capability, if desired. Furthermore, in yet another embodiment, the power to run the light source, spectrometer, and output transmitter may be transmitted from an external source by any of the same processes by which a battery may be recharged.

In an alternative embodiment, there may be no subcutaneously-mounted power supply, but instead a subcutaneous connection port 27 (shown with dashed lines in FIG. 1) may be accessible from outside the body, such as through or othera percutaneous access device may be . In particular, a percutaneous access device such as is described in a U.S. patent application entitled "Percutaneous Access," to Brett Haarala and Paul DiCarlo, assigned to the assignee of this application, filed on the same date as this application, and incorporated herein by reference, may be provided. Connection port 27 may be protrude through the cover of the percutaneous access device, or be accessible by opening the cover of the device. Other subcutaneous data ports known in the art, for example, as described in U.S. Pat. No. 5,205,286 to Soukup et al., incorporated herein by reference, may also be used . In an embodiment that includes a subcutaneous connection port or percutaneous access device, remote monitoring device 30 may connect directly to the subcutaneous electronics package via the connection port, sending power to light source 24, which sends an input optical signal through optical fiber 12a, which returns an output optical signal that is read by spectrometer 26, which provides a signal that is received directly by the remote monitoring device through the connection port. In this way, information from the subcutaneous electronics is communicated to the remote monitoring device. Thus, part or all of the electronics of the present invention may be contained in the cavity defined by the housing of the percutaneous access device described in the Haarala and DiCarlo application. The electronics may be fully contained in the percutaneous access device, with a transmitter 28 such as shown in FIG. 2 for transmitting a data signal, or may only be partially contained, with a physical connection for transmitting data or power protruding through the cover of the device or accessible by opening the device.

In yet another embodiment, only connector 23b and a portion of optical fiber 12a (or connector 23b alone) may protrude from the body or be housed in or accessible through the cover of a percutaneous access device. In such an embodiment, an external light source similar to light source 24 may be used to emit a signal to an optic sensor 22a via the optical fiber itself, and with the spectrometer 26 serving to receive the signal back from the optic sensor. Such a system avoids the need for a transmitter and a receiver, as the information may be directly transferred through optical fiber 12a.

Endoleak Detection

For detection of endoleaks, optical sensor 22a at distal end 14a of optical fiber 12a, as shown in FIG. 1, may comprise a pressure transducer. Optical-fiber-based pressure transducers are known in the art, for example, as manufactured by RJC Enterprises of Woodinville, Wash.; as described in U.S. Pat. No. 6,052,613 to Takaki and assigned to Terumo Cardiovascular Systems Corporation of Somerset, N.J.; or as described in "Fiber-optic Transducer Aids Heart Monitoring," *Engineering News*, Jun. 7, 1999, both of which are incorporated herein by reference. A model FOP-M in-vivo pressure sensor, manufactured by FISO Technologies, of Quebec, Canada, may also be particularly useful for the application of this invention.

In the exemplary embodiment shown in FIG. 1, optical fiber 12b is implanted with its distal end 14b mounted in aneurysm sac 102 of aneurysm 102 and proximal end 16b connected to subcutaneous electronics package 35. Optical fiber 12b in aneurysm sac 102 may be implanted laproscopically. Fiber optic sensor 22b measures the pressure in aneurysm sac 102, and this information is gathered and processed in similar fashion to the information collected by sensor 22a. Although not shown in FIG. 2, fiber 12b may have an independent signal emitter/receiver device or assembly similar to light source 24, coupler 25, and spectrometer 26, or electronics 35 may comprise a single light source with multiple channels and a single spectrometer with multiple channels to serve multiple fibers, each fiber having an associated coupler. Accordingly, the subcutaneous electronics may have a separate transmitter for each fiber, or a single transmitter that transmits multiple channels of information simultaneously. In embodiments including data processing elements such as the a/d converter 44 and CPU/memory 46 within subcutaneous electronics 35, a single channel of information may be transmitted, with bursts of information corresponding to the reading from each fiber transmitted sequentially, or composite information taken from both fibers, such as differential pressure information, may be transmitted.

In an embodiment such as shown in FIG. 1 having both optical fiber 12a integral to prosthesis 10 and an optical fiber 12b integral to aneurysm sac 102, the method of detecting endoleaks comprises monitoring the differential pressure between optic sensor 22a at the end of optical fiber 12a and optic sensor 22b mounted at the end of optical fiber 12b. A differential pressure greater than a threshold pressure or a baseline differential pressure may be interpreted as an indication of an endoleak. Such a baseline or differential pressure may be determined by identifying the value of the pressure differential in a body where it is known that no leaking is occurring.

In another embodiment, a monitoring system may consist of only fiber 12b (with the associated electronics as described above) for measuring only the pressure within aneurysm sac 102. In this embodiment, an initial pressure in the aneurysm sac may be measured soon after placement of the prosthesis and recorded as a baseline pressure when no leaking is occurring. Then, the prosthesis monitoring system is used to take subsequent pressure readings, and the readings are compared to the baseline pressure to determine if there has been any change in pressure. A change from the baseline profile greater than a threshold value may be interpreted as an indication of an endoleak.

Figure 3:
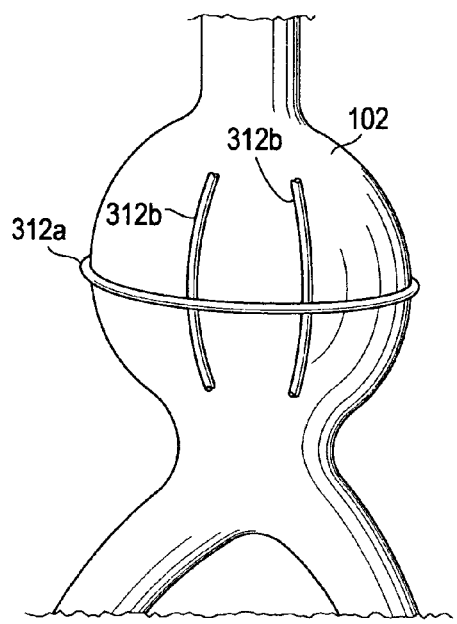
FIG. 3 is an illustration showing exemplary fiber optic placement on an aneurysm sac.

In yet another alternative embodiment, shown in FIG. 3, optical fiber 312a may be implanted laproscopically so that it wraps around the outer surface of aneurysm 102. Spectrometer 26 may be configured to detect changes in the optical signal caused by bending of the optical fiber. The use of optical fibers to detect bending of the fiber is known in the art, for example as described in "Fiber Optic Sensors and Their Applications," by A. Selvarajan, incorporated herein by reference. Optical fiber 312 may then be monitored to determine if it changes its shape or if pulsatile motion (pulsing motion associated with the beating of the heart) is detected, either of which may indicate an endoleak. Additionally, or in the alternative, one or more optical fibers 312b may be laproscopically implanted longitudinally on the outer surface of aneurysm 102 to detect a change in morphology of the aneurysm or pulsatile motion.

Thus, a method of detecting an endoleak may comprise implanting a prosthesis 10, at least one optical fiber, such as 12b (or 12a and 12b), and optionally subcutaneous electronics 35. Switch 34 may be activated to allow power to flow from battery 32 to activate light source 24 to send an input optical signal to fiber optic sensor(s) 22a and/or 22b, each of which returns an output optical signal that is read by spectrometer 26. Spectrometer 26 then communicates with output transmitter 28, and the transmitter transmits information to remote receiver 30. Remote receiver 30 transmits the information to data processor 31 which processes the information. The processed information is then used to determine the pressure or differential pressure, including establishing a baseline pressure or baseline differential pressure and deviance therefrom to indicate an endoleak. In the embodiment shown in FIG. 3, the processed information is used to determine an aneurysm sac morphology baseline and deviance therefrom or to detect pulsatile motion to indicate an endoleak.

Morphology Change Detection

Figure 4:
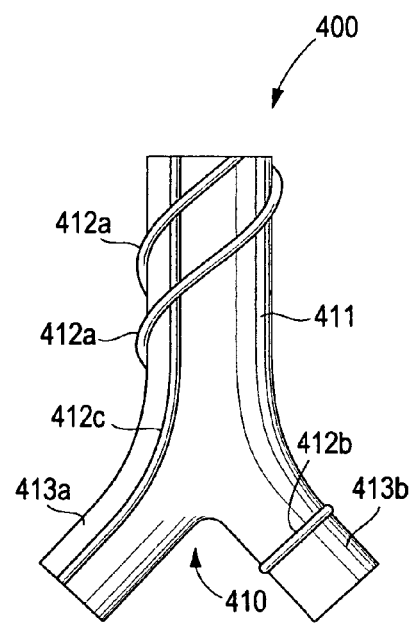
FIG. 4 is an illustration showing exemplary fiber optic placement on a prosthesis.

As shown in FIG. 4, prosthesis 400 comprises one or more optical fibers 412a-c attached thereto. Optical fibers 412a-c may be configured to measure bending of the optical fiber, which may be particularly useful for measuring changing morphology of prosthesis 410. Prosthesis 410 comprises an aortic trunk portion 411 and two iliac leg portions 413a and 413b. The optical fiber may be woven into aortic trunk portion 411, such as helical fiber 412a, or in iliac leg portion such as circumferential fiber 412b. A fiber wound helically, circumferentially, or in any portion of a circumference or helix may also be referred to as a "radial fiber." Fiber 412c that runs along the length of prosthesis 410 may be referred to as a "longitudinal" fiber. Fibers 412a-c may be attached in any number of ways, such as by weaving the fibers within the graft or stent of the prosthesis, sandwiching the fibers between the graft and stent, or bonding the fibers to the graft or stent with an adhesive. Methods of attaching the fibers are discussed in more detail below.

Figure 5:
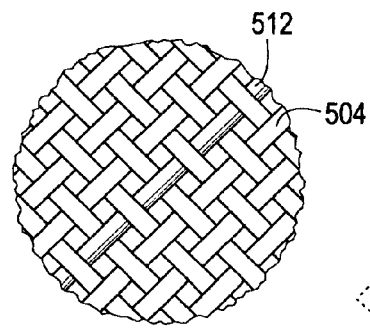
FIG. 5 is an illustration of an optical fiber or an MRI-susceptible fiber woven into a graft or stent.

For a prosthesis comprising a graft referring to FIG. 5, optical fiber 512 may be woven into the graft, with element 504 representing a strand of the graft. Similarly, element 504 may represent a stent filament or strand into which optical fiber 512 is woven. Although shown as a braided architecture in FIG. 5, the stent or graft may comprise any architecture known in the art. For a prosthesis 600 comprising both a graft 604 having an outer surface 610 and an inner surface 612 relative to lumen wall 620, and a stent 602 also having an outer surface 630 and an inner surface 632, the graft may be mounted on the stent inner or outer surface, and the optical fiber may be mounted on the inner or outer surface of the graft or the stent. Accordingly, although shown in an embodiment with optical fiber 614 sandwiched between graft 604 and stent 602 in FIG. 6, the relationships among the graft, stent, and optical fiber may be any of the possible combinations.

Figure 6:
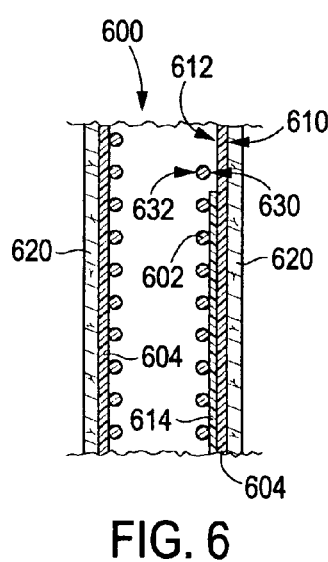
FIG. 6 is a longitudinal cross-sectional illustration of an optical fiber sandwiched between the graft and stent of a prosthesis.

Thus, one exemplary method for detecting a change in morphology of a prosthesis implanted within a body may comprise implanting a prosthesis, such as prosthesis 400, having an integral optical fiber, such as any of fibers 412*a-c*, 512, or 612 shown in FIGS. 4, 5, and 6, respectively, in a lumen, and implanting subcutaneous electronics, such as electronics 35 as shown in FIG. 2, in communication with the integral optical fiber. The information provided by endoluminal device 20 is processed by data processor 31 to establish a prosthesis morphology baseline and deviance therefrom.

Strain Gauge Embodiments

Figure 7B:
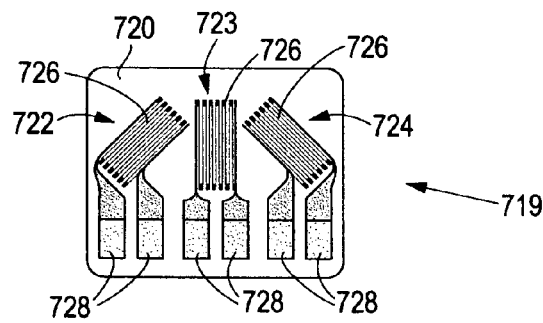
FIG. 7A is an illustration showing an exemplary strain gauge on a prosthesis and FIG. 7B is an enlarged portion of FIG. 7A showing the details of the strain gauge.
Figure 7A:
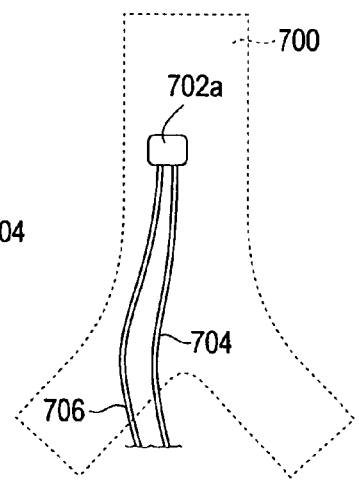
Figure 9:
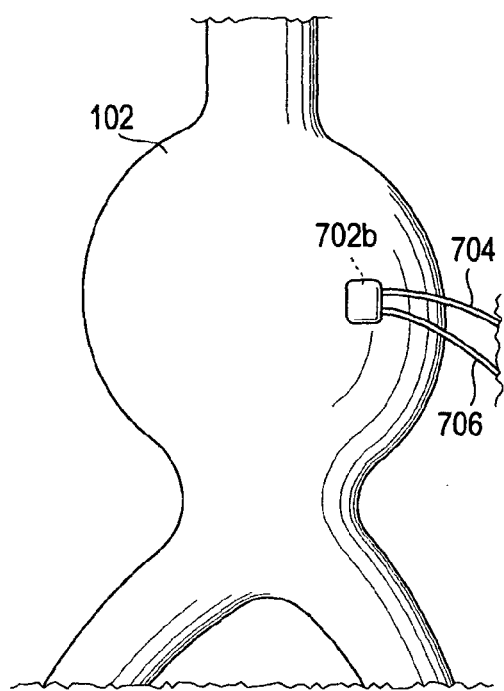
FIG. 9 is an illustration showing an exemplary embodiment including a strain gauge implanted on an aneurysm sac.

In yet another embodiment, shown in FIG. 7A, prosthesis 700 may have an indicator that comprises at least one strain gauge 702*a*, or as shown in FIG. 9, at least one strain gauge 702*b* may be placed on aneurysm sac 102. Strain gauges 702*a* and 702*b* each have a power lead 704 to deliver power to the strain gauge and a signal lead 706 to transmit the strain reading to the electronics. Any type of micro-measurement strain gauge or strain gauge assembly suitable for implantation in the human body may be used. An exemplary strain gauge assembly 719 having a "rosette" design, manufactured by Micro-Flexitronics Limited, of Coleraine, Northern Ireland, is shown in FIG. 7B. Strain gauge assembly 719 comprises a mounting pad 720 on which three individual strain gauges 722, 723, and 724 are mounted. Each individual strain gauge comprises a strain gauge array 726 and a pair of solder pads 728 to which leads (704 and 706 in FIG. 7A) may be attached.

Figure 8:
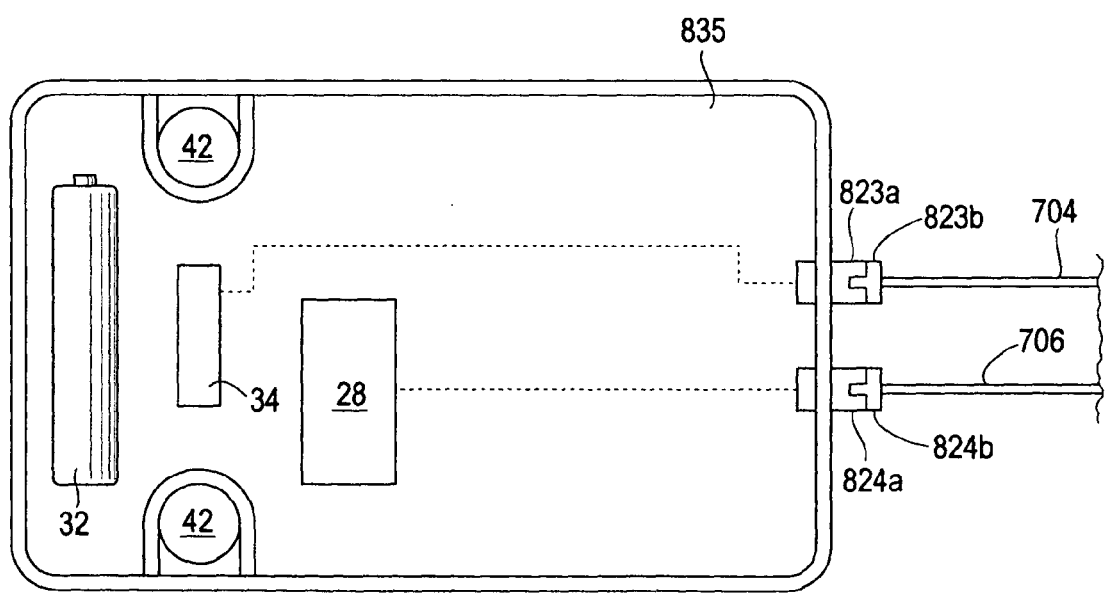
FIG. 8 is a schematic illustration of exemplary subcutaneous electronics for use with a strain gauge.

Similar to the optical fiber embodiments described above, the monitoring system for a strain gauge embodiment preferably includes subcutaneous electronics, similar to electronics 35 shown in FIG. 2, and external electronics 21, including remote receiver unit 130 and data processor 31. For a strain gauge embodiment, however, as shown in FIG. 8, subcutaneous electronics 835 do not include a light source, spectrometer, or coupler, but rather merely include connectors 823*a* and 823*b* and associated wiring for connecting power lead 704 to battery 32 via switch 34 and connectors 824*a* and 824*b* and associated wiring for connecting signal lead 706 to output transmitter 28.

As with the optical fiber embodiments, configurations including subcutaneous data processing electronics, including configurations having continuous operation without a switch but with a battery recharging mechanism; configurations without a subcutaneous battery; configurations without any subcutaneous electronics; or any of the various configurations discussed above or analogous configurations may be provided.

In an embodiment without subcutaneous electronics, one or more integral strain gauges may be implanted, and a connection port, which is connected to power lead 704 and a signal lead 706, may protrude from the lumen and/or from the skin. The connection port may be housed in or on the cover of a percutaneous access device, as described above. To take a reading, a remote monitoring device including data processing electronics 31 is then attached to the connection port, and the monitoring device sends power down power lead 704, enabling the strain gauge to take a reading, and the reading is received through signal lead 706.

Consistent with the general description of the invention, in this embodiment, the indicator device is strain gauge 702*a* or 702*b* and the signal lead 706 serves to convey the signal from the strain gauge to remote monitoring device (data processor 31) that is periodically connected to the signal lead to take the strain gauge reading.

Morphology Change Detection

Figure 10:
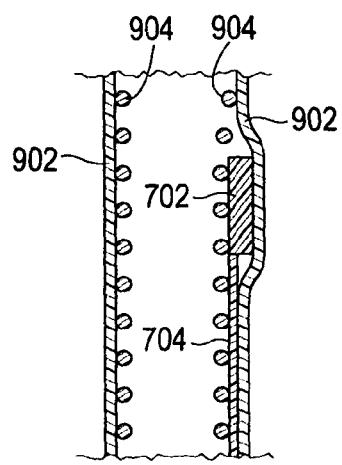
FIG. 10 is a cross-sectional illustration showing a strain gauge sandwiched between the graft and stent of a prosthesis.

Strain gauges may be used for morphology change detection by attaching the strain gauges to or weaving them into the graft in any location along the prosthesis as may be desired, such as in the trunk section, iliac section, or in multiple locations, just as with the optical fibers as described above and shown in FIG. 4. As shown in FIG. 10, strain gauge 702 and leads 704 and 706 (not shown) may be sandwiched between graft 902 and stent 904.

In an exemplary method for detecting a change in morphology of a prosthesis implanted within a body, the method first comprises implanting in a lumen a prosthesis having at least one integral strain gauge 702 and implanting subcutaneous electronics 835. The method then comprises remotely activating switch 34 to allow power to flow from power supply 32 to activate strain gauge 702, which sends a signal to transmitter 28, which transmits information to remote monitoring means 30 which sends the information to data processor 31. The information is used to determine a baseline morphology of the prosthesis and deviation therefrom.

Endoleak Detection

For detection of endoleaks, one or more strain gauges 702 may be mounted laproscopically on the aneurysm sac 102, as shown in FIG. 9. Strain gauges 702 may then be monitored to determine if there is a change in the morphology of aneurysm sac 102 or to detect pulsatile motion of the aneurysm sac, either of which may indicate an endoleak.

MRI-Susceotible Fiber Embodiment

In an embodiment similar to FIG. 5, member 512 within graft or stent 504 may be, instead of an optical fiber, a member that has a magnetic resonance imaging (MRI) susceptibility value that contrasts with the MRI susceptibility value of the remaining stent or graft material. As shown in one embodiment represented by FIG. 5, member 512 is a non-redundant filament within graft 504, but may instead be a redundant "tracer" that runs alongside an structurally integral filament of the graft or stent. The term "magnetic susceptibility" is a dimensionless ratio well-known in the field of MRI, and is comprehensively discussed by Schenck, John F., "The Role of Magnetic Susceptibility in Magnetic Resonance Imaging: MRI Magnetic Compatibility of the First and Second Kinds," *Med. Phys.* 23 (6), June 1996, pp. 815-850, and incorporated herein by reference.

For example, if element 504 is a stent comprising a material having a positive susceptibility value, such as molybdenum having a susceptibility value of $123 \times 10^6$, indicator member 512 preferably comprises a material having a negative susceptibility value, such as gold having a susceptibility value of $-34 \times 10^6$. Conversely, if stent 504 comprises a material having a negative susceptibility value, such as zinc having a susceptibility value of $-15.7 \times 10^6$, indicator member 512 preferably comprises a material having a positive susceptibility value, such as titanium having a susceptibility value of $182 \times 10^6$. Thus, as the orientation of indicator member 512 changes in response to changes in morphology of stent 504, the change in configuration may be readily detected by MRI techniques.

An MRI device may be used for performing a first imaging procedure, from which the results are recorded as a baseline morphology. Then, the MRI device may be used to perform subsequent imaging procedures, where the results of the subsequent procedures are compared to the baseline morphology to determine if there has been any change in morphology.

SUMMARY

Although illustrated and described above with reference to certain specific embodiments, the present invention is nevertheless not intended to be limited to the details shown. Rather, various modifications may be made in the details within the scope and range of equivalents of the claims and without departing from the spirit of the invention.

For example, a prosthesis of this invention may be any such prosthesis having at least one indicator member integral to the prosthesis that is adapted to be remotely monitored to indicate a change in pressure or morphology of the prosthesis. The prosthesis may comprise any stent, graft, or stent-graft architecture known in the art, and is not limited to the exemplary designs shown herein. Although optical fibers, strain gauges, and MRI-susceptible fibers are preferred embodiments, the indicator member may be any member capable of providing the desired result.

Similarly, the prosthesis monitoring systems may comprise any indicator device or assembly affixed to the prosthesis and/or mounted on the aneurysm sac to provide the desired indication. Although optical fibers, strain gauges, and MRI-susceptible fibers are preferred indicators, any means capable of providing the desired result may be used. Particular types of strain gauges and optical fiber sensors or technologies are presented herein only as examples, and are not intended to be limiting. Particular configurations of the subcutaneous and external electronics are also presented herein as exemplary embodiments and are also not intended to be limiting, as any workable combination of electronics may be used to transfer information from the implanted indicators to the remote monitoring means as are known in the art.

Finally, the invention is not limited to the particular methods of analyzing information provided by the monitoring systems discussed herein. Any of the various combinations of components may be used to provide monitoring information that may be used however it is deemed fit to indicate changing prosthesis morphology and endoleaks. Finally, the prosthesis monitoring system may have other useful benefits beyond endoleak and morphology-change monitoring, and thus, the invention is not limited to any particular use.

What is claimed:

1. A monitoring system for an endoluminal device comprising:
   the endoluminal device for implantation in a lumen;
   at least a first optical fiber member having a first end affixed to the endoluminal device and a second end;
   a light source in communication with the first optical fiber at the second end for sending an input optical signal through the optical fiber;
   a spectrometer in communication with the first optical fiber at the second end for receiving an output optical signal from the optical fiber; and
   a transmitter responsive to the spectrometer for transmitting information related to the output optical signal.

2. The monitoring system of claim 1 wherein the prosthesis is deployed to isolate an aneurysm having an aneurysm sac, the system further comprising:
   a second optical fiber having a first end disposed in or on the aneurysm sac and a second end in communication with the light source and the spectrometer.

3. The monitoring system of claim 2 wherein the first optical fiber and the second optical fiber are each configured to measure pressure at the first ends of the first and second optical fibers.

4. The monitoring system of claim 1 wherein the light source, spectrometer, and transmitter comprise subcutaneous electronics adapted to be subcutaneously implanted.

5. The monitoring system of claim 4 wherein the subcutaneous electronics are adapted to be sutured to a portion of skin.

6. The monitoring system of claim 4 wherein the transmitter is adapted to generate an electromagnetic signal or an optical signal transmittable through human skin.

7. The monitoring system of claim 4 wherein the subcutaneous electronics further comprise a battery.

8. The monitoring system of claim 7 wherein the subcutaneous electronics further comprise a remotely-activatable switch for turning power from the battery on and off.

9. The monitoring system of claim 8 wherein the switch is a magnetic switch.

10. The monitoring system of claim 1 wherein the first optical fiber is configured to measure bending of the optical fiber.

11. The monitoring system of claim 1 wherein the first optical fiber is configured to measure pressure at the first end of the optical fiber.

12. The monitoring system of claim 1, wherein the endoluminal device comprises a prosthesis.

13. The monitoring system of claim 1, wherein the endoluminal device comprises a stent, a graft, or a combination thereof.

14. A monitoring system at least partially implantable within a body for detecting a change in morphology of an implanted endoluminal device, the system comprising:
   an indicator affixed to the endoluminal device for indicating a change in morphology of the endoluminal device in a remotely measurable manner; and
   a remote monitoring device for detecting the indication of the change in morphology provided by the indicator;
   wherein the indicator comprises at least one optical fiber.

15. The monitoring system of claim 14 wherein the system further comprises:
   means, in communication with the means for conveying, for sending an input optical signal and receiving an output optical signal from the optical fiber.

16. The monitoring system of claim 14, wherein the endoluminal device comprises a prosthesis.

17. The monitoring system of claim 14, wherein the endoluminal device comprises a stent, a graft, or a combination thereof.

18. A monitoring system at least partially implantable within a body for detecting a change in morphology of an implanted endoluminal device, the system comprising:
   at least one indicator member integral to the endoluminal device that has a first magnetic resonance imaging (MRI) susceptibility value that contrasts with a second MRI susceptibility value of a second material that comprises one or more remaining members of the endoluminal device, the indicator member having a configuration adapted to change in response to the change in morphology;
   a remote monitoring device comprising a magnetic resonance imager adapted to remotely detect the configuration of the member to detect the change in the indicator member effected by the change in morphology; and means for conveying information from the indicator member to the remote monitoring device.

19. The monitoring system of claim 18, wherein the endoluminal device comprises a prosthesis.

20. The monitoring system of claim 18, wherein the endoluminal device comprises a stent, a graft, or a combination thereof.

21. The monitoring system of claim 18, wherein the first material of the indicator member has a positive MRI susceptibility value and second material of the one or more remaining members of the prosthesis has a negative MRI susceptibility value.

22. A prosthesis monitoring system at least partially implantable within a body for detecting an endoleak in an implanted prosthesis, the system comprising:
   an implantable indicator for indicating a change in pressure attributable to an endoleak, the indicator comprising at least one optical fiber;
   means for sending an input optical signal and for receiving an output optical signal through the optical fiber; and
   remote monitoring means for detecting the indication of the change in pressure provided by the indicator.

23. The prosthesis monitoring system of claim 22 wherein the indicator is integral to the prosthesis.

24. The prosthesis monitoring system of claim 23, wherein the prosthesis comprises an aortic trunk and at least one iliac leg and the indicator member is integral to the at least one iliac leg.

25. The prosthesis monitoring system of claim 22 wherein the prosthesis is adapted to be deployed to isolate an aneurysm having an aneurysm sac and the indicator is adapted to be disposed in the aneurysm sac.

26. The prosthesis monitoring system of claim 22 wherein the prosthesis is adapted to be deployed to isolate an aneurysm having an aneurysm sac and the indicator comprises a first optical fiber member adapted to be mounted (a) in the aneurysm sac to detect pressure or (b) on the aneurysm sac to detect (b)(i) a change in morphology of the aneurysm sac or (b)(ii) pulsatile motion of the sac.

27. The prosthesis monitoring system of claim 26 wherein the indicator consists of only the first optical fiber member.

28. The prosthesis monitoring system of claim 22 wherein the prosthesis is adapted to be deployed to isolate an aneurysm having an aneurysm sac and the indicator comprises a first optical fiber member adapted to be mounted in the aneurysm sac to detect pressure, and a second optical fiber member affixed to the prosthesis and that is adapted to detect pressure, the system further comprising means for sending a first input optical signal and receiving a first output optical signal through the first optical fiber and sending a second input optical signal and receiving a second output optical signal through the second optical fiber.

29. A monitoring system at least partially implantable within a body for detecting a change in pressure or morphology of a prosthesis, the prosthesis comprising a graft and a stent having a compressed configuration for introduction into the body and an expanded configuration for deployment in the body, the system comprising:
   an indicator sandwiched between the graft and the stent in the expanded configuration for indicating a change in morphology of the prosthesis in a remotely measurable manner, wherein the indicator comprises a strain gauge; and
   a remote monitoring device for detecting the indication of the change in morphology provided by the indicator.

30. A monitoring system at least partially implantable within a body for detecting a change in pressure or morphology of a prosthesis, the prosthesis comprising a graft and a stent having a compressed configuration for introduction into the body and an expanded configuration for deployment in the body, the system comprising:
   an indicator sandwiched between the graft and the stent in the expanded configuration for indicating a change in morphology of the prosthesis in a remotely measurable manner, wherein the indicator comprises a first material having a first magnetic resonance imaging (MRI) susceptibility value that contrasts with a second MRI susceptibility value of a second material that comprises one or more remaining members of the prosthesis; and
   a remote monitoring device for detecting the indication of the change in morphology provided by the indicator.

31. A prosthesis monitoring system at least partially implantable within a body for detecting a change in pressure or morphology of an implanted prosthesis, the system comprising:
   the prosthesis, comprising an aortic trunk and at least one iliac leg;
   an indicator member affixed to the iliac leg of the prosthesis for indicating a change in morphology of the prosthesis in a remotely measurable manner, wherein the indicator member is adapted to be remotely monitored to indicate a change in pressure or morphology of the prosthesis, the indicator member comprising an optical fiber, a strain gauge, or a first material having a first magnetic resonance imaging (MRI) susceptibility value that contrasts with a second MRI susceptibility value of a second material that comprises one or more remaining members of the prosthesis; and
   a remote monitoring device for detecting the indication of the change in morphology provided by the indicator.

32. The monitoring system of claim 31, wherein the indicator member is woven into the iliac leg of the prosthesis.

33. The monitoring system of claim 31, wherein the first material of the indicator member has a positive MRI susceptibility value and second material of the one or more remaining members of the prosthesis has a negative MRI susceptibility value.

* * * * *